United States Patent
Lanting et al.

(10) Patent No.: US 7,708,885 B2
(45) Date of Patent: May 4, 2010

(54) ANAEROBIC DIGESTION APPARATUS, METHODS FOR ANAEROBIC DIGESTION AND FOR MINIMIZING THE USE OF INHIBITORY POLYMERS IN DIGESTION

(75) Inventors: Jelte Lanting, Sewell, NJ (US); John L. Murphy, III, Voorhees, NJ (US)

(73) Assignee: Biothane LLC, Camden, NJ (US)

( * ) Notice: Subject to any disclaimer, the term of this patent is extended or adjusted under 35 U.S.C. 154(b) by 0 days.

(21) Appl. No.: 12/228,136

(22) Filed: Aug. 8, 2008

(65) Prior Publication Data

US 2008/0302721 A1 Dec. 11, 2008

Related U.S. Application Data

(63) Continuation of application No. 10/161,387, filed on May 31, 2002, now abandoned.

(60) Provisional application No. 60/294,805, filed on May 31, 2001.

(51) Int. Cl.
*C02F 3/28* (2006.01)

(52) U.S. Cl. .................... 210/603; 210/613

(58) Field of Classification Search ......... 210/603, 210/609, 612, 613; 71/10; 435/262, 262.5
See application file for complete search history.

(56) References Cited

U.S. PATENT DOCUMENTS

| | | |
|---|---|---|
| 3,787,316 A | 1/1974 | Brink et al. |
| 4,165,285 A | 8/1979 | Wind et al. |
| 4,267,038 A | 5/1981 | Thompson |
| 4,284,510 A | 8/1981 | Savard et al. |
| 4,290,884 A | 9/1981 | Mandt |
| 4,301,007 A | 11/1981 | Savard et al. |
| 4,377,066 A | 3/1983 | Dickinson |
| 4,446,018 A | 5/1984 | Cerwick |
| 4,488,960 A | 12/1984 | Goerlich |
| 4,551,250 A * | 11/1985 | Morper et al. ............ 210/603 |
| 4,609,460 A | 9/1986 | Vellinga |

(Continued)

FOREIGN PATENT DOCUMENTS

DE 24 00 416 A 7/1975

(Continued)

OTHER PUBLICATIONS

PCT Notification of transmittal of the International Search Report and International Search report (PCT/US02/17398), 4 pages (Sep. 27, 2002).

(Continued)

*Primary Examiner*—Fred Prince
(74) *Attorney, Agent, or Firm*—Flaster/Greenberg, P.C.

(57) ABSTRACT

The invention includes an anaerobic solids digestion apparatus comprising a digester, at least one draft tube; at least one nozzle and a biogas source; a method for digesting a waste stream in an anaerobic solids digestion apparatus comprises feeding a waste stream to a digester; reacting the anaerobically biodegradable material in the waste stream with anaerobic bacteria in the digester; introducing a mixed liquor into the digester and mixing the mixed liquor; and a method for minimizing the use of inhibitory polymers by concurrently digesting and concentrating the mixed liquor in the digester.

27 Claims, 6 Drawing Sheets

U.S. PATENT DOCUMENTS

| | | | |
|---|---|---|---|
| 4,618,418 A | 10/1986 | Heijnen et al. | |
| 4,659,464 A | 4/1987 | Long, Jr. | |
| RE32,597 E | 2/1988 | Pette | |
| 4,749,494 A | 6/1988 | Tomoyasu et al. | |
| 4,885,094 A | 12/1989 | Srinivasan et al. | |
| 4,940,546 A | 7/1990 | Vogelpohl et al. | |
| 4,954,257 A | 9/1990 | Vogelpohl et al. | |
| 5,116,505 A | 5/1992 | Lourens et al. | |
| 5,120,442 A | 6/1992 | Kull et al. | |
| 5,185,079 A * | 2/1993 | Dague | 210/603 |
| 5,230,794 A | 7/1993 | Heijnen et al. | |
| 5,360,546 A | 11/1994 | Tomita et al. | |
| 5,409,610 A | 4/1995 | Clark | |
| 5,454,949 A | 10/1995 | Davis et al. | |
| 5,505,862 A | 4/1996 | Sonnerein | |
| 5,518,618 A | 5/1996 | Mulder et al. | |
| 5,565,098 A | 10/1996 | Vellinga | |
| 5,616,240 A | 4/1997 | Sonnenrein | |
| 5,616,288 A | 4/1997 | MacDonald | |
| 5,739,031 A | 4/1998 | Runyon | |
| 5,811,259 A | 9/1998 | Hall | |
| 5,837,141 A | 11/1998 | Vogelpohl | |
| 5,855,785 A | 1/1999 | Heijnen et al. | |
| 5,942,118 A | 8/1999 | Besten | |
| 5,945,039 A | 8/1999 | Kojima | |
| 5,948,261 A | 9/1999 | Pressley | |
| 5,993,650 A | 11/1999 | Kim | |
| 6,030,534 A | 2/2000 | De Lima | |
| 6,059,971 A | 5/2000 | Vit et al. | |
| 6,224,769 B1 | 5/2001 | Hasegawa et al. | |

FOREIGN PATENT DOCUMENTS

| | | | |
|---|---|---|---|
| DE | 31 02 435 A1 | | 10/1982 |
| DE | 31 17 461 A1 | | 11/1982 |
| DE | 31 17 462 A1 | | 11/1982 |
| DE | 31 44 487 A1 | | 5/1983 |
| DE | 32 31 234 A1 | | 3/1984 |
| DE | 32 44 577 A1 | | 6/1984 |
| DE | 33 23 514 A1 | | 1/1985 |
| DE | 34 13 537 A1 | | 10/1985 |
| EP | 0 130 499 A1 | | 1/1985 |
| EP | 0 808 805 A1 | | 11/1997 |
| JP | 58-214396 A | * | 12/1983 |
| JP | 61-4598 A | * | 1/1986 |
| JP | 61-178016 A | * | 8/1986 |
| JP | 7-96298 A | * | 4/1995 |
| WO | WO 95/13990 A1 | | 5/1995 |

OTHER PUBLICATIONS

Waste Water Engineering: Treatment, Disposal, and Reuse, Metcalf and Eddy, Inc., 1991, pp. 780,801-810.

* cited by examiner

PRIOR ART-SLUDGE PROCESSING ACCORDING TO CONVENTIONAL METHODS

FIG. 4

SLUDGE PROCESSING ACCORDING TO ONE EMBODIMENT OF THE INVENTION

ANAEROBIC DIGESTION APPARATUS, METHODS FOR ANAEROBIC DIGESTION AND FOR MINIMIZING THE USE OF INHIBITORY POLYMERS IN DIGESTION

CROSS-REFERENCE TO RELATED APPLICATIONS

This application is a continuation of U.S. patent application Ser. No. 10/161,387, filed May 31, 2002, which in turn claims priority under 119(e) to Provisional Patent Application 60/294,805, entitled "Shear Enhanced Anaerobic Digestion Apparatus," filed May 31, 2001, the contents of each of which are incorporated herein by reference.

BACKGROUND OF THE INVENTION

The invention relates to anaerobic biological treatment of waste streams with high solids content. Anaerobic biological treatment has traditionally been applied to the digestion of primary and secondary sludge at municipal sewage treatment facilities, but is also applicable to municipal solid waste, agricultural manures and crop residues, or industrial solid wastes and slurries where a significant portion of the solids material is potentially biodegradable.

Anaerobic digestion of municipal sludge has been performed for decades to reduce volume, stabilize highly-putrescible material and destroy pathogens. Conventional digestion is a once-through process where the sludge resides in the digester for 20 to 40 days to achieve optimal digestion. This is expressed as solids retention time (SRT) which in a once-through system is equal to the hydraulic retention time (HRT). SRT represents the average time that solids reside in the digester, and HRT represents the average time that liquids reside in the digester. In order to optimize the digestion process and to reduce the size of the digester vessel, there is a need for an improved digestion method that can operate effectively at a reduced SRT.

One problem associated with municipal sludge digestion is the large volume required for the anaerobic digester. Concentrating the solids in municipal sludge upstream of the digester has been used for reducing the digester volume. Even though municipal sludge is relatively high in suspended solids compared to many industrial wastewaters, typically approximately 99% of the municipal sludge may be water. To achieve the conventional SRT, the digester must accommodate the volume of water in the sludge. By concentrating these sludge solids by a factor of two, the digester volume required for digestion could be halved. Traditionally, a thickening process has been applied upstream of the digester to increase the percentage of solids in the feed to the digester. Traditional methods involve mechanical thickeners, dissolved air flotation or similar equipment to concentrate the solids.

Additives, such as polymers, have been mixed with the sludge stream to enhance the thickening process. These polymers are known in the art and include, for example, cationic polyacrylamides in a water-in-oil emulsion, solution mannich polymers—nonionic polyacrylamide polymers made cationic by reacting the amide groups along the polyacrylamide backbone with both a dialkylamine and a formaldehyde source, and cationic water-soluble polymers in emulsions, for example polyamine or poly (diallyldialkylammonium halides). The applicants have discovered that such polymers can inhibit anaerobic biological digestion. This effect might not be noticeable in conventional systems with long SRT and relatively low biological activity. However, as the digestion process is optimized and the SRT is reduced, this impact becomes more noticeable and prevents achievement of optimal digestion performance.

Less conventional methods for thickening the sludge such as membrane separation have also been used upstream of the digester. However, the hydrophilic nature of the solids in the waste stream makes it difficult to extract water efficiently using a membrane separator and promotes fouling of membranes, a build up of colloidal hydrophilic compounds which is difficult to penetrate and disturb. Traditionally, this made membrane separation an unattractive method for thickening the waste stream. Thus, in order to optimize anaerobic sludge digestion, there is a need for an improved method of concentrating the feed stock delivered to the digester and eliminating the need for the above noted polymers in optimized digesters.

Digesters for the anaerobic digestion of municipal publicly-owned treatment works (POTW) sludge are generally large tanks of relatively low height providing for 20-40 days of HRT. Proper treatment of municipal POTW sludge requires a sufficient inventory of active digesting bacteria and contact of those bacteria with the biodegradable fraction of the sludge. Contact is achieved by mixing digester contents. Optimally, the digester contents are mixed thoroughly. Conventional mixing methods include mixing by mechanical methods and mixing by using gas. However, the large and low design of conventional digesters typically results in "dead zones" which are not mixed and which could reach or exceed approximately 15% of the digester.

An "egg-shaped" digester has been developed to address these problems. This shape has improved the overall performance by effectively approaching a 100% mixed digester volume. This digester also requires a smaller widest cross-sectional area because it is taller relative to the traditionally-shaped tanks noted above. However, construction of egg-shaped digesters must overcome complex geometry. Although they are smaller than conventional digesters, they are still relatively large and expensive to construct. These structures improve mixing efficiency, but remain limited by the solids retention time (SRT) dictated by their design parameters and the typical biological activity of a continuously stirred system.

Accordingly, there also remains a need for improved digester performance by exposing more surface area of the degradable organics and available digesting bacteria to increase the opportunity for reactions between them. One way to achieve this is to fragment the sludge particles so as to expose degradable organics and digesting bacteria on the interior of the particles. These components may then be brought into contact in a high-energy environment. This requires turbulent mixing in the digester.

One method of mixing in an anaerobic sludge digester is the loop digester. Loop digesters have a continuous circulating flow which may be around a draft tube configuration. A mixing method used in the field of aerobic digestion is the concept of an eductor nozzle immersed in a liquid filled vessel. The pressure on the pumped side of the nozzle can be used to accelerate the flow of liquid at the nozzle outlet thus releasing energy into the liquid filled vessel and disturbing the vessel contents to effect mixing. Additionally, this acceleration creates a suction effect (similar to a Venturi) which can be used to draw a secondary fluid or gas into the flow stream.

Eductor nozzles to fragment biological solids have been used in the treatment of wastewaters using high rate aerobic digesters that apply a shearing force to the mixed liquor in the digester. With the supplemental addition of oxygen in the form of air injection, these digesters rely on contact between wastewater and biomass particles in an oxygen-rich environment to promote aerobic bacterial digestion of soluble components contained in the wastewater.

Another problem associated with municipal sludge is its disposal. Regulatory restrictions on the disposal of sludge make it desirable that the sludge be treated to "Class A" standards prior to disposal. 40 CFR § 503.32 proscribes EPA standards regarding the use and disposal of sewage sludge and is incorporated herein by reference. Accordingly there is a need for an improved digester design that can provide for operational or process modifications that achieve sludge which is treated to Class A standards.

BRIEF SUMMARY OF THE INVENTION

The invention includes an anaerobic solids digestion apparatus comprising a digester; a mixing device in the digester capable of directing a flow of a mixed liquor within the digester; and a shearing device in communication with a mixed liquor inlet to the digester, the shearing device being capable of imparting shear to a mixed liquor within the digester.

The invention also includes an anaerobic solids digestion apparatus comprising a digester comprising a shear source capable of imparting shear to a mixed liquor within the digester and a concentrator in fluid communication with a mixed liquor inlet of the digester and at least one mixed liquor outlet of the digester, wherein the concentrator and digester are configured to allow for concurrent concentration and digestion of a mixed liquor.

The invention also includes an anaerobic solids digestion apparatus comprising a digester; at least one draft tube positioned in the digester and capable of directing a flow of a mixed liquor and comprising an upper inlet and a lower outlet; at least one nozzle comprising a gas inlet, a liquid inlet, an outlet and an interior surface, the nozzle further comprising a gas tube having an exterior surface, the tube extending from the nozzle gas inlet to the nozzle outlet, wherein a generally annular space is defined between the exterior surface of the gas tube and the interior surface of the nozzle; and a biogas source in communication with the gas inlet of the nozzle.

The invention additionally includes a method for digesting a waste stream in an anaerobic solids digestion apparatus, the method comprising feeding a waste stream comprising anaerobically biodegradable solids to a digester; reacting the anaerobically biodegradable solids in the waste stream with anaerobic bacteria in the digester to reduce an amount of the biodegradable solids, thereby producing a mixed liquor and a biogas; introducing a mixed liquor to the digester through a shearing device; and mixing the mixed liquor within the digester.

The invention includes a method for improving the efficiency of an anaerobic solids digestion apparatus comprising feeding a waste stream comprising anaerobically biodegradable solids to a digester; reacting the anaerobically biodegradable solids in the waste stream with anaerobic bacteria in the digester to reduce an amount of the biodegradable solids, thereby producing a mixed liquor and a biogas; imparting a shearing force to the mixed liquor in the digester; and concentrating the mixed liquor, wherein the steps of reacting the anaerobically biodegradable solids and concentrating the mixed liquor occur concurrently.

The invention additionally includes a method for minimizing the need for use of a polymer that inhibits biological activity in a waste stream in a digestion apparatus, the method comprising feeding a waste stream to a digester, wherein a portion of the waste stream is biodegradable; reacting the biodegradable portion in the waste stream with bacteria in the digester to produce a mixed liquor and gas; and concentrating the mixed liquor with a membrane separator, wherein the steps of reacting the biodegradable portion in the waste stream and concentrating the mixed liquor occur concurrently.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

DETAILED DESCRIPTION OF THE INVENTION

The present invention relates to an apparatus, designated generally in the drawings as 100, and process for the anaerobic digestion of solids in a waste stream using a shear enhanced anaerobic digestion apparatus (SEAD). The invention also relates to an apparatus and method for concurrently concentrating and digesting the degradable solids fraction of a waste stream. The invention additionally relates to a method of minimizing the need for use of a polymer(s) that can inhibit biological activity in a waste stream. By utilizing a preferred continuous recirculating flow around a draft tube, mixing of the system can be achieved without moving parts within the digester. A shearing nozzle may be used in the apparatus to impart energy to the digester contents so as to fracture solids particles and expose the maximum reactable surface area. When energy is released through the nozzle, the fluid inside the draft tube is accelerated, resulting in about a ten-fold increase in internal flow rates compared to the recirculation flow, as described further herein. Shearing of the particles in the waste stream or waste slurry solids, occurs both within the nozzle, as well as in a turbulent mixing zone at the outlet of the nozzle, physically breaking down the solid biodegradable particles of the waste stream or waste slurry into smaller particles, exposing more surface area of the biodegradable solids. Biogas produced in the anaerobic digestion can be recycled in the two-phase nozzle and mixed with the mixed liquor. Entrained biogas is dispersed throughout the circulating mixed liquor providing for maximum turbulence in the mixed liquor to ensure optimal contact of the biodegradable organics with the anaerobic bacteria. These factors improve mass transfer rates resulting in significantly improved reaction efficiency evidenced by reduced SRT.

A fraction of the digester contents can be concentrated by using membrane separation or other conventional concentration process in combination, and preferably concurrently, with the digestion apparatus. A concentrator is in fluid communication with an inlet and an outlet of the digester, so that the concentrator and digester may operate concurrently. As digestion acts on the degradable waste material in the digester, the hydrophilic components are being digested, and the digester contents are more easily concentrated. Because the apparatus can work alongside a concentrator, they can be operated concurrently and the thickening of the waste is significantly improved. Thus, the design of the apparatus including a concentrator as described herein enhances separation performance over conventional concentration processes with the result that the feed stock to the digester is effectively concentrated. Additionally, the performance of the digester is enhanced because the concentration can be performed without the need for the use of polymers that can inhibit biological activity or other additives that can negatively impact an optimized digester such as the digester described herein. Applicants have additionally discovered that concurrently concentrating while digesting the feed stock for other types of digesters, including, for example, non-shear enhanced anaerobic digesters, egg-shaped anaerobic digesters, and aerobic digesters, can also minimize the need for additives, such as thickening polymers that may act to inhibit biological activity in those digesters when optimized.

In general, waste streams to be treated according to the various embodiments and aspects of the present invention may be any waste streams containing material that is at least partially biodegradable by anaerobic or aerobic bacteria. However, the principle aspects of the invention are directed to anaerobic bacteria unless otherwise specified herein. Preferably, such waste streams are primary and/or waste-activated sludge from municipal sewage treatment plants or industrial aerobic wastewater treatment plants, but may also include wastewater streams from solid waste agricultural manures, crop residues, industrial solid wastes, sludge, and slurries or any other high solids waste streams where a significant portion of the solids material is potentially biodegradable. The present invention can process streams with high concentrations of total suspended solids (TSS) and/or fat, oil and grease (FOG), as well as the slurries or solid waste having anaerobically digestible material.

In a preferred embodiment of the invention represented in the attached Figures, the waste stream is preferably a waste slurry. More preferably, the waste slurry is a mixture of primary and secondary sludge in a ratio of about 70:30 to about 30:70, most preferably about 60:40 to 40:60. In the case of waste sludge, a total solids concentration of about 2 to about 20 wt % is preferred for embodiments of the digester of the invention without the concentrator based on the weight of solids divided by the weight of the sample. For embodiments of the digester with the concentrator, the total solids concentration is preferably about 1 to about 10 wt %, more preferably about 1 to about 5%. About 60 to about 90 wt % of the solids present in such waste sludge are generally volatile, potentially biodegradable solids. The waste sludge will also preferably have an inlet chemical oxygen demand (COD) level of at least 20,000 mg/l for the embodiments of the digester of the invention without the concentrator and at least 5,000 mg/l, more preferably at least 10,000 mg/l, for embodiments of the invention with concentrator. For waste slurries, COD levels of greater than 2,000 mg/l are preferred. It will be understood, however, based on the disclosure that the anaerobically digestible stream processed by the invention can have varied characteristics.

The following is a detailed description of preferred embodiments of the invention and should not be considered to be limiting. The referenced schematics in FIGS. 1-6 are representative and not drawn to scale. Certain terminology is used in the following description for convenience only and is not considered to be limiting. The words "lower" and "upper", "top" and "bottom", "upward" and "downward" and "left" and "right" designate directions in the drawings to which reference is made. The terminology includes the words specifically mentioned, derivatives thereof and words of similar import.

Figure 1:
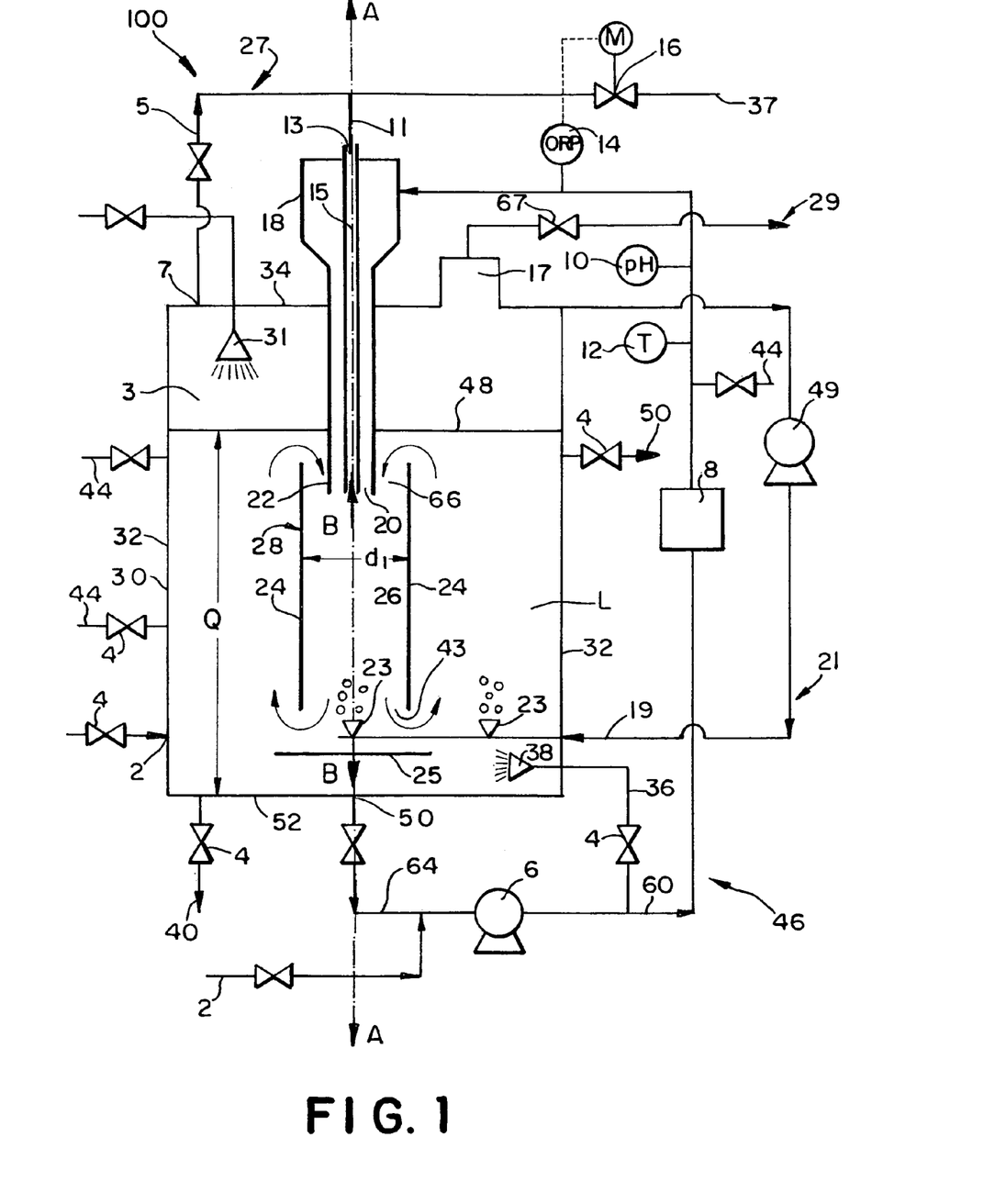
FIG. 1 is a schematic representation of the features of a shear enhanced anaerobic digestion apparatus according to the invention.

A waste stream can be introduced into a digester 30, as shown in FIG. 1, through one or more inlets 2 located around the periphery of the digester vessel or through the digester recirculation conduit 60, 64 as described herein. The digester 30 also preferably includes one or more mixed liquor outlets 50 around the periphery of the digester vessel, one of which may serve as a main outlet for discharging digester effluent or the digested liquor or sludge for disposal or further processing. The digester may also include one or more sample ports 44 around the periphery of the digester. The digester 30 additionally may include one or more drains 40 for emptying the vessel when not in use. The term "mixed liquor" in this specification includes, but is not limited to a mixed liquor, a mixture of solids, liquids and gas and the biodegradable portion therein and bacteria therein, which in the preferred embodiment are anaerobic bacteria. The mixed liquor may be within the digester, fed into the digester as a recycle stream from the digester and any effluent from the digester.

Preferably, the digester volume is selected such that the sludge retention time SRT within the digester is about 2 to about 20 days, preferably about 6 to about 12 days. The configuration of the digester may vary, however, preferably it is a generally cylindrical vessel with a height as measured along the longitudinal axis A of the digester of preferably about 25 feet (8 m) to about 75 feet (23 m), and more preferably about 45 feet (14 m) to about 55 feet (17 m), with a height to diameter ratio of about 0.2 to about 20, and more preferably about 1 to about 4, wherein the diameter is measured in a transverse direction along the largest transverse dimension of the digester. The digester can be constructed of any conventional material that is consistent with the materials handling and structural requirements of the particular materials to be digested and digester design chosen. However, it is preferable that the digester is constructed of concrete, steel or fiberglass.

As shown in FIG. 1, the waste stream is preferably fed to the digester upstream of a recirculation pump 6. The digester inlet 2 is preferably upstream of the digester recirculation pump 6 so that the feed immediately and intensely contacts with the digesting bacteria existing in the preferred recirculated stream flowing through conduit 60 and is mixed proportionately with that stream. In the preferred embodiment, the waste stream is fed continuously to the digester 30, although a batch feeding operation may also be utilized. The rate of feed of waste stream into the digester may vary, but the maximum feed rate can generally be determined by dividing the volume of the digester employed by the design hydraulic retention time (HRT).

Preferably the digester is operated at a controlled mixed liquor volume, which is a substantially constant volume, subject to typical control fluctuations. To maintain the mixed liquor volume inside the digester at a controlled volume, an amount of mixed liquor substantially equal to the flow rate of the waste stream feed is extracted from the digester 30 via a mixed liquor outlet 50, preferably one located to extend generally transversely from a side 32 of the digester vessel. A control valve 4, such as a gravity overflow or control valve, or any other appropriate flow control mechanism can be used to control the mixed liquor discharge so as to maintain the liquid volume in the digester at a substantially constant volume.

Figure 2:
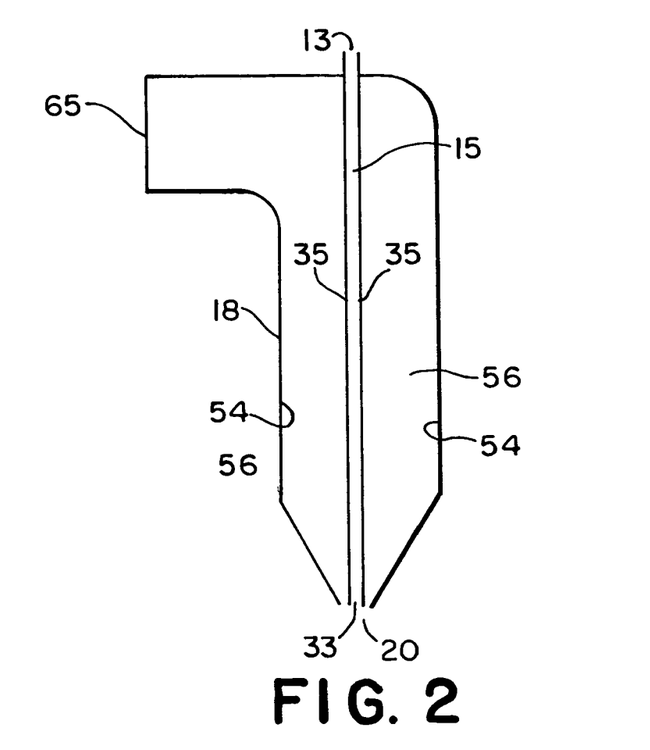
FIG. 2 is a schematic representation of a two-phase mixing and shearing nozzle.
Figure 5:
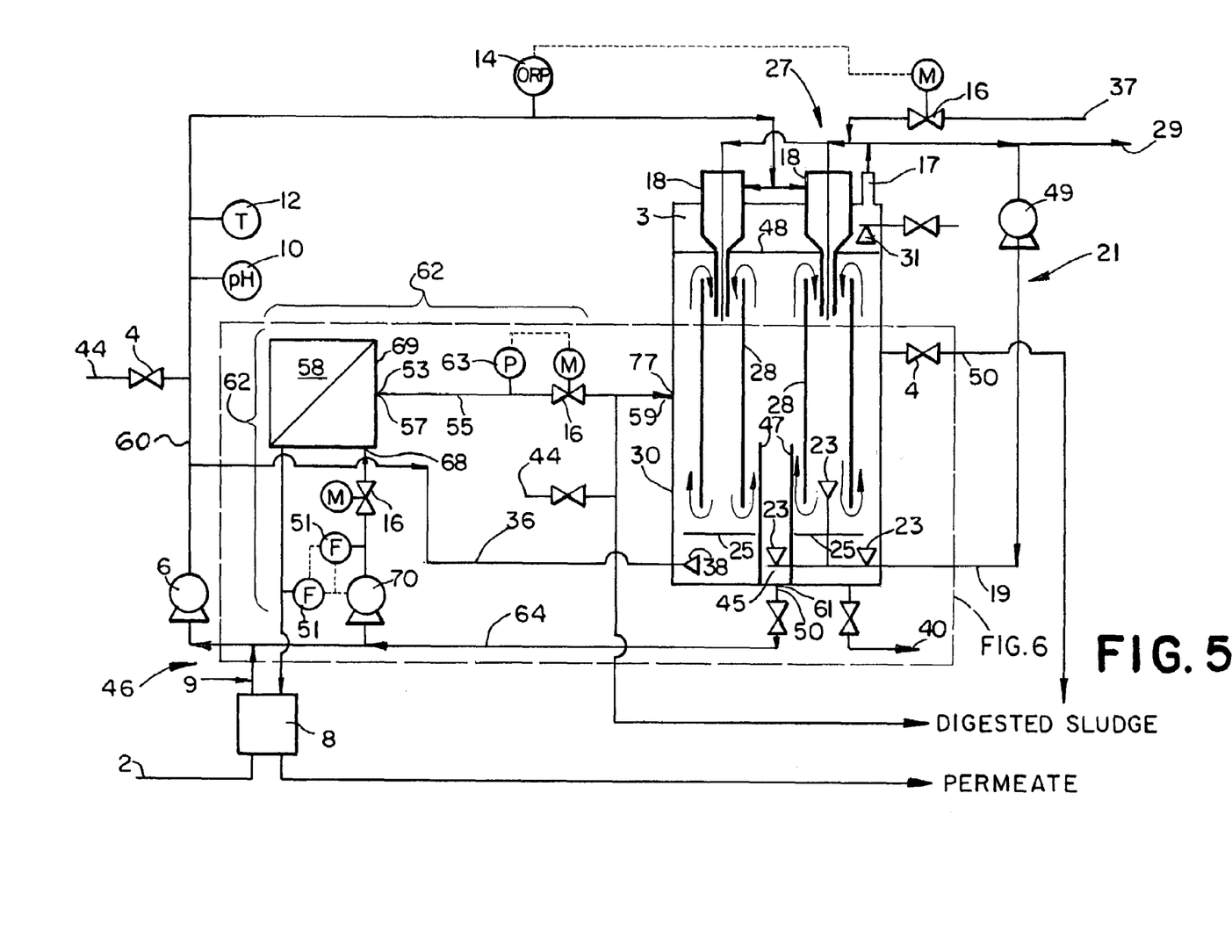
FIG. 5 is a schematic representation of an anaerobic digestion apparatus and a membrane concentrator.

In the preferred embodiments illustrated in FIGS. 1 and 5, the apparatus further includes a recirculation system 46, including the recirculation pump 6 and recirculation conduit 60, 64. The recirculation system provides fluid communication for the mixed liquor L within the digester 30 from a mixed liquor outlet 50, which in this instance serves as a mixed liquor recirculation outlet, preferably in the bottom 52 of the digester vessel, to a liquid inlet 65 of at least one preferred two-phase nozzle 18 as best shown in FIG. 2. In the preferred embodiment, the rate of recirculation through the recirculation system is controlled to be substantially constant such that the digester volume divided by the digester volume recirculation rate is about 15 to about 150 minutes, and more preferably about 45 to about 75 minutes. Similar digester recirculation rates would be preferred in the processing of other waste slurries such as agricultural or industrial slurries. However, recirculation rates can be altered or optimized for varying systems. A first conduit 60 conveys liquid from pump 6, which may be a pump or any liquid pumping apparatus that moves the liquid through the conduit 60, 64, to the liquid inlet 65 of the nozzle 18. A second conduit 64 conveys liquid from the mixed liquor outlet 50 that serves as the mixed liquor recirculation outlet to the pump 6. It is understood that the term "conduit", as described in this specification, may be any pipe, conduit, tube, conveyance mechanism, valve, or indirect or direct connection or the like which provides fluid communication as described herein.

If the inlet 2 is connected to the second conduit 64, the recirculation system 46 provides a continuous blend of waste stream feed and recirculated mixed liquor from the digester to the liquid inlet 65 of the preferred two-phase nozzle 18 which would then discharge fresh waste stream and recirculated mixed liquor and biogas from a biogas source into the digester 30. The nozzle 18, best shown in FIG. 2, includes a nozzle gas inlet 13 in fluid communication with a biogas source, a nozzle liquid inlet 65 and a nozzle outlet 20. The nozzle further has a gas flow tube 15 extending from the nozzle gas inlet 13 to the gas tube outlet 33 in proximity to the nozzle outlet 20. A nozzle space 56 which is generally annular is defined by the exterior surface 35 of the gas flow tube 15 and the interior surface 54 of the nozzle 18, through which recirculated mixed liquor is passed.

As illustrated in FIG. 1, the pump 6 circulates the recirculation stream and/or feed stream and pressurizes the slurry upstream of the preferred two-phase nozzle 18. The pump energy is transferred to the digester contents at the fluid outlet 20 of the preferred two-phase nozzle 18. The fluid outlet 20 of the preferred two-phase nozzle 18 is configured such that the nozzle annular space 56 narrows at the nozzle outlet causing an acceleration of the mixed liquor at the outlet. The velocity gradient generated via the nozzle outlet 20, is preferably maintained at a level of about 50 to about 500 $\sec^{-1}$, as defined by formula (I)

$$G=(P/(\mu V))^{0.5} \quad \text{(I)}$$

wherein G is the mean velocity gradient, $\sec^{-1}$, P is the power requirement in Watts, V is the digester volume in cubic meters, and $\mu$ is the dynamic viscosity of the digester contents in $Ns/m^2$.

The energy transferred to the mixed liquor at nozzle outlet 20 imparts a shearing force on the solids in the stream which breaks the solids into smaller particles and increases the surface area. The increase in surface area exposes more unreacted organics making them accessible to the anaerobic bacteria. The shearing occurs both inside the nozzle 18 as the fluid is accelerated and in the mixing zone 66 outside the nozzle outlet 20 where the energy of the mixed liquor is transferred to the digester contents.

Figure 2A:
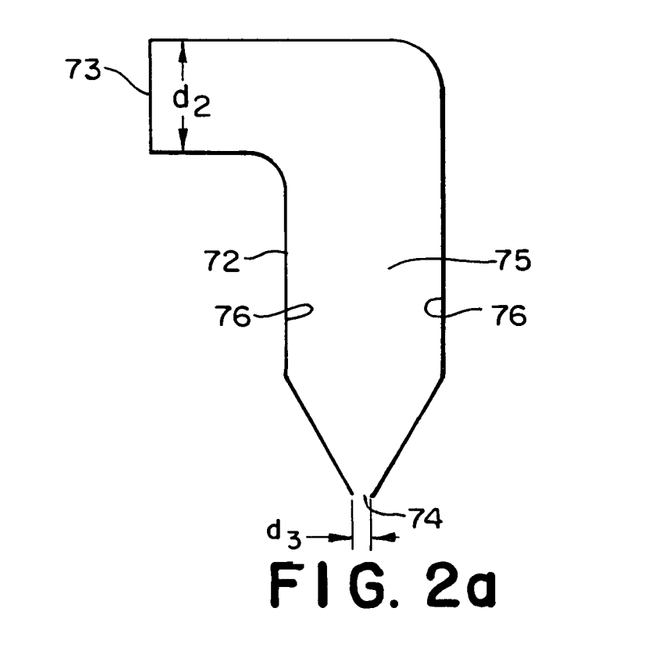
FIG. 2a is a schematic representation of a single phase mixing and shearing nozzle.

In the preferred embodiment, the nozzle is a two-phase nozzle which can provide a shearing force as well as educting a gas. However, it will be recognized by one skilled in the art that a single phase nozzle 72, as shown in FIG. 2a, would also be suitable for the providing shear to the mixed liquor in the digester. The nozzle in FIG. 2a includes a liquid inlet 73 having a diameter $d_2$, which would be in fluid communication with a mixed liquor outlet 50 of the digester 30 shown in FIG. 1, and a liquid outlet 74 having a diameter $d_3$ which is narrower than the diameter $d_2$ of liquid inlet 73 for introducing mixed liquor into the digester, wherein the diameters $d_2$ and $d_3$ are measured in the largest dimension and transversely across openings 73 and 74, respectively. The narrower outlet 74 causes acceleration of the mixed liquor at the outlet 74. Recirculated liquor passes through an interior space 75 of the nozzle 72 defined by interior walls 76 of the nozzle 72. Unlike the two phase nozzle 18 described above, the single-phase nozzle 72 does not include a gas tube. Additionally, other types of shearing devices, for example a Venturi valve or nozzle, or an impeller, capable of fracturing the solids and introducing them into the digester while not as preferred as the nozzles of the present invention may also be used within the scope of the invention.

The number of nozzles used can vary depending upon the volume of the digester and/or the desired optimized process. For example, two nozzles are shown in the preferred embodiment of FIG. 5. Preferably, about one nozzle to about 150 to about 1,500 cubic meters of digester volume is preferred, and more preferably about one nozzle to about 600 to about 900 cubic meters of digester volume.

A "mixing device" which is preferably a draft tube but may be any mixing device including impellers, injected gas, vacuum pumping, mixing blades and the like capable of inducing mixing within the digester are within the scope of the invention. It will be recognized by one skilled in the art that other forms of mixing such as mechanical mixers or gas injection or other mixing methods in the presence of a shear enhanced medium would contribute to an improvement in mass transfer rates and, accordingly, be suitable for use in the invention. As best shown in FIG. 1, the nozzle outlet 20 discharges proximate to the inlet 22 of a draft tube 28 positioned below the level 48 of the mixed liquor in the digester. The fluid exiting the nozzle flows downwardly through the inner area 26 defined by the draft tube 28. The diameter $d_1$ of the draft tube 28 as measured transversely through the tube is preferably constant and is preferably about 40 to 200 centimeters. Preferably the length $l_1$ of the draft tube 28 as measured along a longitudinal axis B of the draft tube should be such that the draft tube inlet 22 is sufficiently far below the surface of the liquid level to allow circulation of the contents of the digester into the draft tube inlet 22, as shown in FIG. 1, and the draft tube outlet 43 is sufficiently far above the bottom of the digester to minimize flow restriction or excessive pressure drop. More preferably the length $l_1$ of the draft tube 28 ranges from about 50% to about 90% of the digester liquid depth Q as measured longitudinally from the bottom 52 of the digester to the surface 48 of the mixed liquor, with the depth of the liquid above the draft tube inlet being no greater than the liquid depth below the draft tube outlet 43. It is understood that more than one draft tube may be employed according to the considerations discussed above with respect to the number of nozzles employed. A 1:1 relationship between the number of nozzles employed and the number of draft tubes employed is preferred. However, there may be more than one nozzle per draft tube in the anaerobic digestion apparatus according to the invention.

The continuing downward flow of the nozzle effluent into the draft tube 28 induces a generally downward flow inside the draft tube. As the mixed liquor exits the draft tube outlet 43, it is forced upwardly by the digester bottom such that a circulation pattern is developed within the digester 30 in which liquid flows back up around the exterior surface 24 of the draft tube 28 and then is pulled and/or pushed downwardly again into the draft tube 28 through the upper inlet 22. This induced circulation pattern around the draft tube preferably exceeds the volumetric flow rate discharged from the nozzle and is beneficial to the mixing of the mixed liquor, and more preferably the enhanced circulation is about 5 to about 25 times the discharge volumetric flow rate of the nozzle. The enhanced mixing provided by the preferred circulation around the draft tube contributes to an increased mass transfer rate.

The degree of anaerobic digestion of a particular biodegradable solid substrate is limited by the organic makeup of that substrate. However the rate at which this digestion can be achieved is affected by the mass transfer rate. By improving the mass transfer rate, a reduction in the time for achieving digestion can be effected. The induced circulation of the mixed liquor within the digester 30 provides enhanced mixing of the digester contents thoroughly dispersing the feed material and exposing the unreacted organics to the digesting bacteria. Because the shearing effect of the nozzle 18 has increased the exposed surface area of the unreacted organics, the mass transfer rates of the anaerobic digestion process are improved over conventional anaerobic digesters. Under the influence of the energy imparted to the digester by the discharge from nozzle 18, these conditions increase the mass transfer rate.

The anaerobically biodegradable material contained in the waste stream is digested through reactions in the digester 30, where anaerobic bacteria convert the biodegradable material to a biogas which substantially is made up of methane and carbon dioxide, with lesser amounts of other gases, such as hydrogen sulfide. These gaseous components and other similar anaerobic gas byproducts are generally referred to herein as "biogas". The biogas may also contain small amounts of water vapor, nitrogen and traces of other volatile compounds which may be present in the feed or formed during biodegradation. The composition of the biogas by volume percent will vary depending on the particular digestible organics being processed. Preferred methane levels in biogas formed in the digester of the invention are in the range of about 50 to about 90 volume percent. Preferred carbon dioxide levels are in the range of about 5 to about 45 volume percent and hydrogen sulfide levels can range from about 200 parts per million (volume) to about 6 volume percent. Action of the anaerobic bacteria on the digestible organics also results in multiplication of the anaerobic bacteria.

This apparatus preferably has a biogas source in fluid communication with the nozzle 18 to provide biogas to the nozzle 18. A preferred biogas source is a biogas recycle system generally designated 27 which uses a portion of the gas generated in digestion as gas feed to the nozzle. However biogas or other anaerobic digestion feed gas can be introduced independently through inlet 37 and/or used together with a biogas recycle system as shown in FIG. 1. Below the upper surface 34 of the digester, the level 48 of the mixed liquor is such that there is an area 3 above the liquor to allow for collection of the biogas that de-entrains from the mixed liquor at its upper surface 48. The volume of the area 3 above the mixed liquor may vary, but there is preferably a distance of about 4 feet (1 m) to about 7 feet (2.5 m), more preferably about 5 feet (1.5 m) to about 6 feet (2 m), of space between the upper surface 48 of the mixed liquor and the upper surface 34 of the digester 30 to prevent any foam that is generated from impeding circulation or gas collection. This biogas collection area 3 is preferably in fluid communication with nozzle 18 in a biogas recycle system. Preferably, the biogas recycle system is provided for recycling a portion of the biogas from the collection area 3 to the nozzle 18. More preferably this biogas recycle system 27 comprises a conduit 5. The conduit provides an outlet at one end 7 for biogas in the collection area 3. The other end 11 of the conduit is in communication with the gas inlet to the nozzle. The conduit preferably has a control valve 4 for adjusting the rate of flow of the biogas in the conduit 5. Biogas is also preferably vented from the collection area, for example via a defoaming hood 17 through biogas outlet 29, with such venting preferably being controlled, for example by a further valve 67, to maintain a gas pressure in the area 3 of about atmospheric pressure to about 50 inches water at 35° C. (12,400 Pa). More preferably, the pressure range will be about 10 inches water at 35° C. (2,500 Pa) to about 20 inches water at 35° C. (5,000 Pa). Any biogas not recycled through the biogas recycle system 27 may be discharged and may subsequently be burned as fuel or utilized for other purposes.

In addition to biogas, additional gases may be introduced to the nozzle 18 through inlet 37. For example, nitrogen feed gas may be routed to the nozzle 18, either for control of strippable toxins, or for altering the carbon dioxide equilibrium between the biogas and the mixed liquor, thereby affecting the pH of the mixed liquor in the digester. Alternatively, small amounts of air or oxygen may be routed to the nozzle 18 through inlet 37 or a separate gas inlet (not shown) to modulate the oxidation-reduction potential (ORP) of the mixed liquor. This is desirable since the tendency of undesirable anaerobic bacterial reactions to produce hydrogen sulfide is favored by particular ranges of oxidation-reduction potential. Hydrogen sulfide is malodorous, corrosive to certain materials, and toxic to humans and the digesting bacteria. By adjusting the oxidation-reduction potential of the mixed liquor to a region outside those favoring hydrogen sulfide production, the level of hydrogen sulfide present in the mixed liquor may be reduced, thereby mitigating one of the less desirable features associated with anaerobic digestion. This may be facilitated by an ORP meter or gauge 14 coupled to the SEAD system 100, preferably somewhere along the recirculation system 46, most preferably along the conduit 60. This ORP meter or gauge 14 may signal a motorized control valve such as valve 16 to adjust the flow of gas from inlet 37.

As previously described, the mixed liquor is accelerated as it exits the nozzle 18, which is in close proximity to the outlet 33 of the gas flow tube 15. This creates an eduction effect useful for the preferred biogas recycle system which draws the biogas and removes a portion of the biogas from the biogas collection area 3, through nozzle 18, and introduces the portion of biogas into the digester 30. As the mixed liquor and the biogas exit the nozzle 18, further mixing occurs between the portion of biogas and the recirculating mixed liquor at the nozzle outlet 20 and the outlet 33 of the gas flow tube with the gas creating increased turbulence at the nozzle discharge. This turbulence exerts an additional shearing force on the solid particles in the mixed liquor, further fracturing particles and thereby providing additional surface area of degradable organics. This additional shearing mechanism further enhances the performance of the invention by providing for increased mass transfer rates as described above when more of the degradable organics are exposed.

Increase of the mass transfer rate in the anaerobic process requires an increase in the exposed surface area available to the digesting bacteria as well as thorough mixing to assure that mass transfer reactions can occur at an optimum rate. The eduction of the portion of biogas removed from the gas collection area 3 into the recirculating mixed liquor stream at the nozzle 18 entrains fine gas bubbles in the mixed liquor circulating inside the digester 30. Because the gas velocity differs from the fluid velocity of the mixed liquor in both the draft tube 28 interior 26, where the mixed liquor is flowing downward carrying the entrained gas by overcoming its buoyancy, and in the area outside the draft tube 28, where the velocities of the mixed liquor and gas are both upward but different, the entrained gas promotes a high degree of turbulence on the sheared particles in the mixed liquor. In conjunction with the induced circulation imparted by the nozzle 18 and draft tube 28, this entrained gas turbulence further promotes an increase in the mass transfer rate that is beneficial to the optimum performance of the invention.

As discussed above, the eduction effect of the nozzle draws biogas into the mixed liquor from a biogas source, preferably the biogas recycle system 27. It is preferred to control the amount of biogas recycled into the mixed liquor, for example by control valve 4 on conduit 5. In the preferred embodiment the volume ratio of biogas to liquid in the nozzle will be up to about 0.5 of the volume of biogas per volume of liquid that flows through the nozzle. However, it is recognized that the characteristics of each mixed liquor will vary for many reasons including the characteristics of the feed waste stream and it is further recognized that these characteristics will impact the rate at which entrained gas generated within or injected into the mixed liquor is released. It is also recognized that as the mass transfer rate of the digester 30 is increased, the rate at which biogas is generated within the mixed liquor mammoth stream due to the digestion process also increases. At such point in the operation of the system where the volume of biogas entrained in the mixed liquor due to digestion has reached the level sufficient to provide the amount of gas turbulence preferred for the given application, the biogas recycle may be shut off by closing control valve 4.

The concentration of solids in the waste stream feed is expressed in percent total suspended solids (TSS). In the illustration case of municipal POTW waste sludge, the TSS of the feed before thickening is typically less than 1.0% TSS. Typically this sludge is thickened to about 5% TSS by utilizing polymers in the thickening process. The applicants have discovered that performance of an optimized digester, such as the apparatus of the invention, can be negatively impacted by the presence of such thickening polymers in the waste stream. Digesting the unthickened waste stream would effect this, but the digester volume would become proportionally larger which is not desirable. Thus a method to thicken the waste feed without the need for polymer addition is desired.

Figure 3:
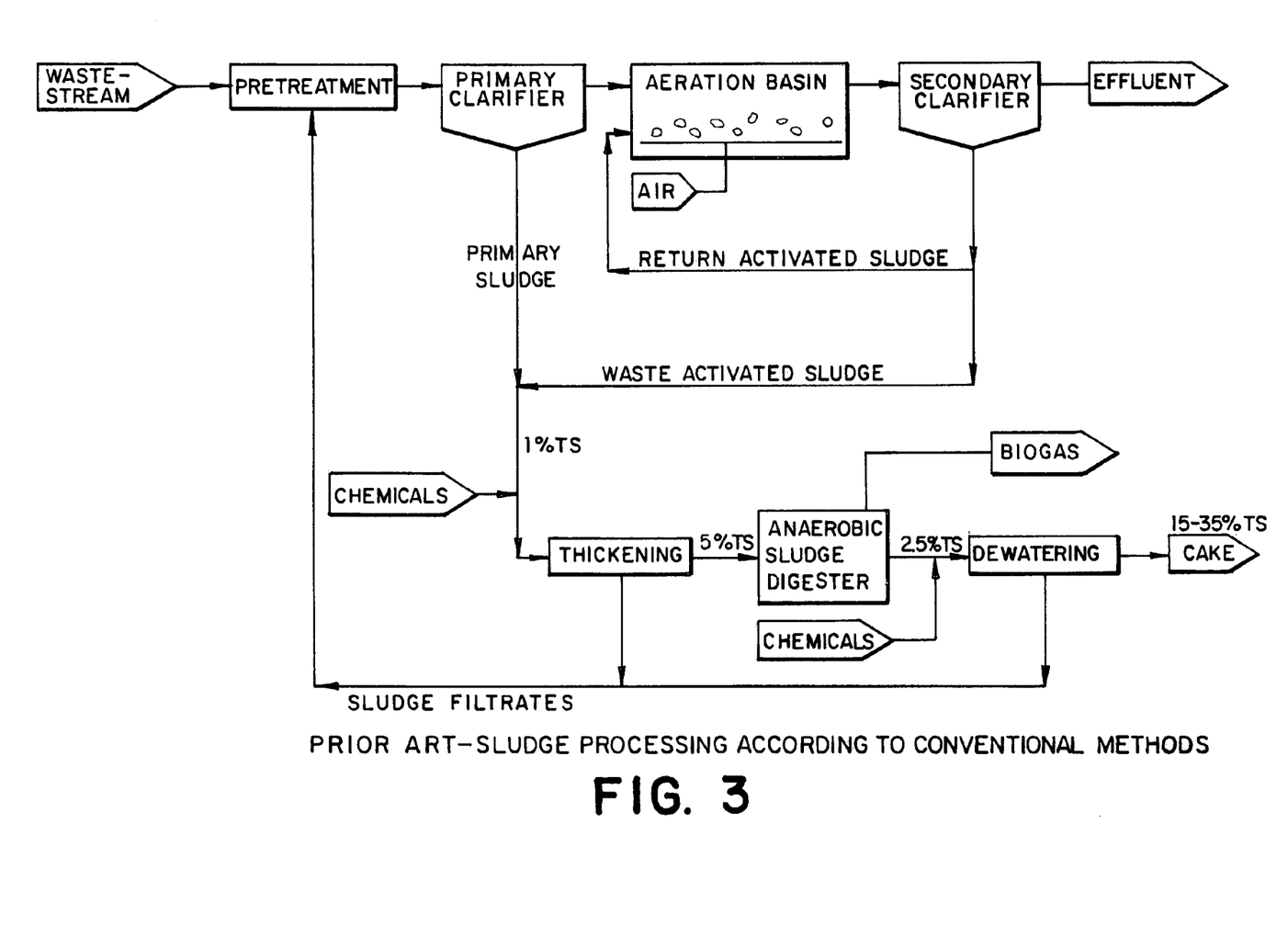
FIG. 3 is a schematic representation of a conventional sludge treatment process.

In conventional digestion processes, of which FIG. 3 is representative, concentration or thickening of the feed into the digester occurs upstream of the digester. However, conventional methods typically do not digest the hydrophilic compounds in the waste stream. The hydrophilic compounds typically present in the solids in the waste stream make it difficult to thicken. The performance of any concentration system, and in particular a membrane concentrator, can be improved if the hydrophilic compounds can be removed from the medium as these compounds reduce the tendency of the medium to release water. The digester apparatus of the present invention will digest these hydrophilic compounds and, when operated concurrently with the concentrator, enhances the performance of the concentrator by removing these hydrophilic compounds that make it difficult for the concentrator to thicken.

Figure 4:
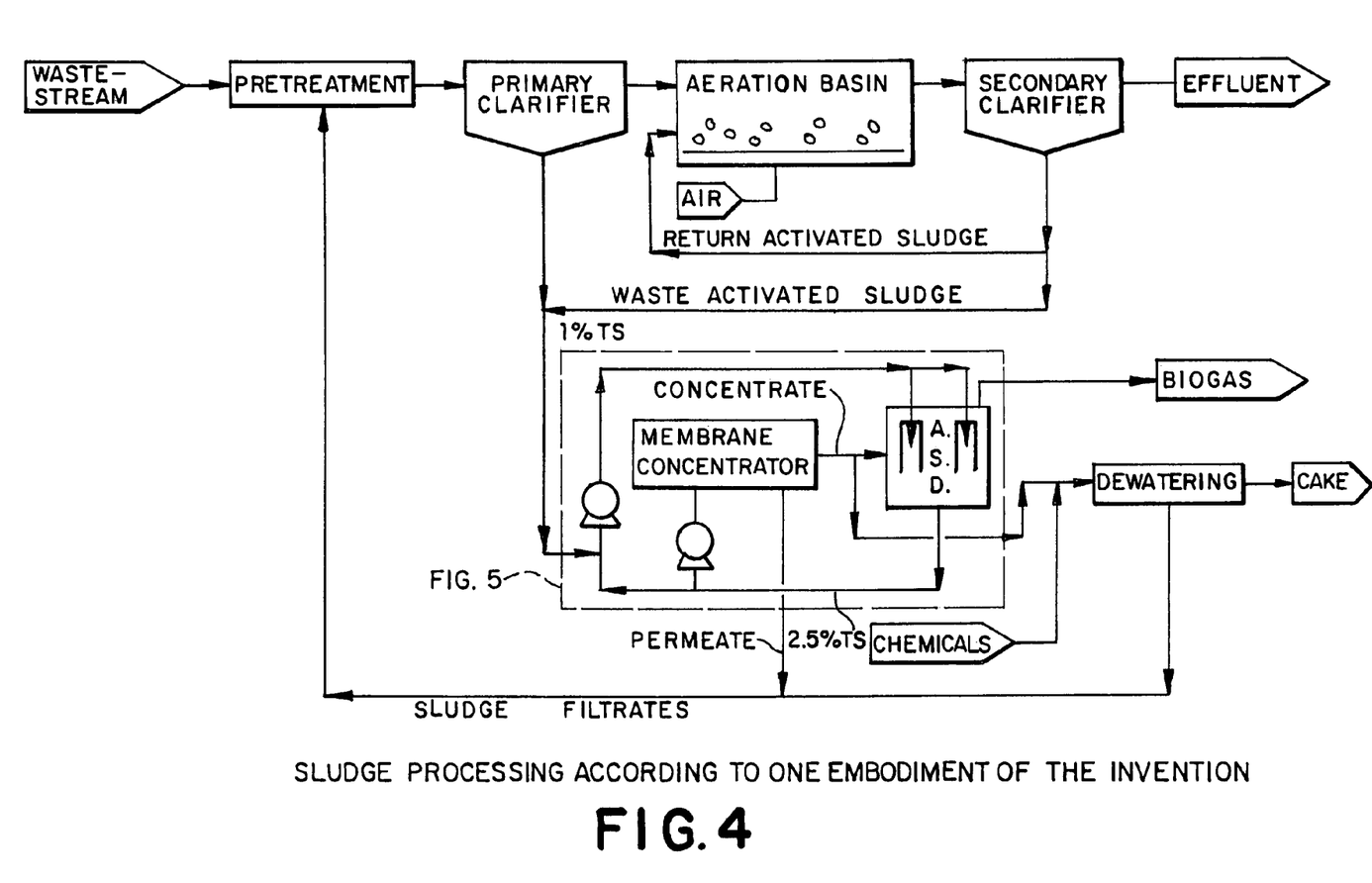
FIG. 4 is a schematic representation of a sludge treatment process according to an embodiment of the invention which includes a membrane concentrator.

As shown in FIGS. 4 and 5, in a preferred embodiment of the invention, a concentrator 62 conveys a portion of the mixture of solids and liquid from a mixed liquor outlet 50 of the digester, preferably the mixed liquor recirculation outlet, to the concentrator and back to an inlet 77 of the digester. The concentrator 62 is in fluid communication with an inlet 77 and with a mixed liquor outlet 50 of the digester. More preferably, the concentrator comprises a pump 70, which may be the pump 6 of the recirculation system, but is preferably one or more separate pumps, and a separator 58 having an outlet 53 which is in fluid communication with an inlet 77 of the digester and an inlet 68 in communication with a mixed liquor outlet 50 of the digester. The concentrator also preferably includes a conduit 55 with a first end 57 connected to the outlet 53 of the separator 58, and a second end 59 connected to the inlet 77 of the digester. This conduit preferably conveys the concentrate from a concentrate side 69 of the separator 58 back to the digester 30.

Most preferably, the separator is a water-permeable membrane including and preferably manufactured of a material suitable for processing a liquid with various concentrations of suspended solids and suspended solid particles of varying sizes. An example of a suitable membrane is an ultra-porous, asymmetric, polymeric ultra-filtration membrane. Commonly used polymers include cellulose acetates, polyamides, polysulfones, poly (vinylchloride-co-acrylonitrile)s, and poly (vinylidene fluoride). Membrane separation is an effective concentrating method, however, other concentration methods such as a lamella separators, dissolved air flotation, gravity belt filter, decanter, rotating screen, or others are suitable separators. The permeate from the concentrator and any unused concentrate may be discharged from the system or routed to one or more heat exchangers 8 as discussed below.

If desired, a flow control meter(s) or gauge(s) 51 and preferably a motorized valve 16 may be provided to control the flow of mixed liquor to and from the concentrator. However, any control mechanism is acceptable for controlling the flow of liquor to and from the concentrator. Additionally, a pressure meter or gauge 63 coupled with a motorized valve 16 may be employed to control the pressure of mixed liquor conveyed to the digester 30 from the separator 58. However, any pressure control mechanism is suitable for controlling the pressure of the mixed liquor conveyed to the digester.

The digester configuration described previously allows for improved rates of digestion due to increased mass transfer rates but the volatile solids destruction is limited by the fraction of biodegradable solids available in said waste stream and is a function of solids retention time (SRT). The process performance in the same apparatus can be further improved if the SRT of the digester can be extended without increasing the digester volume. This can be achieved by further increasing the solids concentration in the digester. With the apparatus of the preferred embodiment, concurrent concentration and digestion allows for adjustment of the mixed liquor concentration resulting in increased SRT in the digester at a fixed waste stream feed rate. Thus the design SRT can be targeted to achieve a particular goal such as, for example, to increase volatile solids destruction or to achieve specific effluent solids concentration. Applicants have discovered that concurrent concentration and digestion in the above manner using a membrane separator not only minimizes or eliminates the need to use the potentially inhibitory polymers in optimized digesters, including the various embodiments of the apparatus of the invention, but in any digester, including non-shear enhanced anaerobic digesters, egg-shaped anaerobic digesters, and aerobic digesters.

The preferred embodiment is illustrated for the case of a municipal POTW waste sludge or a waste slurry. Similar digester designs and use of this method are envisioned for digesting other waste slurries from agricultural and industrial sources by the present invention. It is recognized that the percent fraction of biodegradable material in the slurry will vary based on the source and also that the concentration of solids in the slurry could be in the range of about 0.5% to about 12% TSS, but is preferably above 1% TSS. It is further recognized that the treatment objectives or economics of a given application might make it preferable to operate the digester 30 or concentrator 62 at parameters outside of the preferred ranges. Considering these factors it is recognized that in some applications concentration of the feed may not be required and, in fact, a dilution stream might instead be preferred to achieve the desired mixed liquor TSS in the digester. It is also recognized that this anaerobic digestion process will also digest the soluble biodegradable organics present in the fluid stream. These and other variations in the present invention are contemplated.

An optional gas de-entrainment zone 45 can be provided within the digester 30, as shown in FIG. 5. The gas de-entrainment zone is preferably in the form of a vertical cylinder defined by a wall(s) 47 with an open top and a closed bottom 61, preferably contiguous with the bottom 52 of the digester, except for an opening in the bottom 52 which is in communication with a mixed liquor outlet 50 of the digester, preferably the mixed liquor recycle outlet. The shape of the wall(s) 47 of the zone may be generally cylindrical or otherwise configured so that the transverse cross sectional area of the zone is sufficient such that the downward velocity of the mixed liquor in the zone caused by the suction of the recirculation pump 6 is less than the rate of rise of gas bubbles of less than about 1 mm in diameter, in order to allow for such bubbles to de-entrain from the mixed liquor. The preferred cross sectional area varies, but should be sufficient such that the downward velocity of the mixed liquor in the entrainment zone may range from 0.02 to 0.2 m/s, more preferably 0.05 to 0.1 m/s. This gas de-entrainment zone is preferred to avoid any potential for such gas bubbles to contribute to possible cavitation at the recirculation pump or the concentrate pump 6, which could result in mechanical damage.

Alternatively, an optional gas deflector plate 25, depicted in FIGS. 1 and 5 is preferably positioned between the lower outlet 43 of the draft tube 28 and the digester bottom 52 to minimize the entrainment of gas bubbles in the mixed liquor at the point where it enters the conduit 50 of the recirculation system 46 or the concentrator 62. Generally there is no limitation on the shape or materials of construction of the plate. Preferably the gas deflector plate 25 has a shape that is larger than the outlet of the draft tube but smaller than a size that would cause the downward velocity of the mixed liquor flowing around the plate 25 to be increased above the rise rate of gas bubbles less than about 1 mm in diameter, in order to allow for such bubbles to de-entrain from the mixed liquor. It is understood however that, optional gas de-entrainment zone and deflector plate may used each alone or in combination in varying SEAD systems according to the invention.

Performance of the system can be further enhanced by operating the system at optimal levels of pH. Any conventional manual or automated pH control mechanism can be used to control and optimize these conditions inside the digester. In such cases a conventional pH control system 10 can be included, preferably in the recirculation conduit 60, to measure pH and dose appropriate amounts of adjusting chemicals. The preferred pH level of the digester for the anaerobic digestion is about 6 to about 8. For certain waste slurries, such as those with a chemical oxygen demand (COD) below 30,000 mg/l, adjustment of the pH may be required to maintain the optimum level in the digester.

Performance of the system can also be further enhanced by operating the system at optimal levels of temperature. Any conventional temperature control mechanism may be used to control the temperature of the mixed liquor in the digester. One mechanism, shown in FIG. 1, includes a temperature meter or gauge 12 and a heat exchanger 8, preferably in the recirculation system 46 of the invention. A preferred method, shown in FIG. 5, includes the use of a heat exchanger 8 and a steam injector 9 upstream of recirculation pump 6. As shown in FIG. 5, the heat exchanger 8 may serve as a recovery heat exchanger to capture heat from the permeate from concentrator 62. The waste heat may also be recovered from the digester effluent or the excess concentrate using a separate heat exchanger (not shown). The temperature control mechanism preferably heats the feed into the digester (or into the recirculation conduit) to a temperature at or slightly above the preferred reaction temperature prior to the entry of the mixed liquor and/or feed into an inlet 2 of the digester. The preferred temperature level of the digester for mesophilic anaerobic digestion is about 80° F. (25° C.) to about 105° F. (40° C.). The digester may also be operated in the thermophilic range of about 125° F. (50° C.) to about 145° F. (60° C.). However, the feed into the digester may be heated to any temperature that does not damage the anaerobic bacteria to a degree that negatively impacts the digestion process. In the case where it is preferred to destroy pathogens in the slurry, such as for the purpose of producing Class A municipal sludge, operation in the thermophilic range would allow for achievement of this objective simultaneously with digestion of the degradable organics.

As described herein, the recirculation of mixed liquor through the nozzle 18 induces a circulation pattern around the draft tube 28, which provides for mixing of the digester contents. In addition, the biogas entrained in the mixed liquor enhances the mixing. In addition to the beneficial effects mixing and turbulence heretofore mentioned, mixing provides a more uniform pH and temperature profile across the digester, thereby maintaining stable reaction conditions within the digester vessel.

It has been found advantageous for the desired operability of the shear enhanced anaerobic digestion apparatus and process to provide elements to allow the successful restart of the digester operation after an extended shutdown. On shutdown, solid material tends to settle in the digester 30, potentially building into a layer with a depth sufficient to block at least the outlet of the draft tube 28. The solids buildup inhibits restart of the digester operation since, absent remedial efforts, the solids have a tendency to remain stationary, thereby blocking the pump suction and the draft tube 28, as well as potentially blocking the inlet feed. It has been found that by providing liquid circulation in the bottom of the digester, it will disturb any layer of built-up solids sufficiently to improve liquid circulation within the digester 30 and assist start-up. As shown in FIGS. 1 and 5, preferably, the liquid circulation would be supplied by pump 6 and a conduit 36 in fluid communication with the discharge of the pump 6 and a nozzle 38 on the digester 30, and would be directed below the deflector plate(s) 25 or otherwise in the area above and in proximity to the digester bottom 52. This liquid circulation may have any shape that sufficiently disturbs the layer of built up solids.

In the event that the liquid circulation is not sufficient to clear the draft tube 28 of solids build up or in lieu of the liquid circulation, an additional biogas recycle system 21, may be utilized. The biogas recycle system 21, preferably includes internal gas nozzles 23, in communication with a conduit 19, to force a gas upwardly around and into the draft tube 28 so as to dislodge the solids, before beginning normal operation of the nozzle 18. The system may also be further facilitated by an optional pump 49 to accelerate the flow of gas to nozzles 23.

It has also been found desirable to use a defoaming spray system for the optimum operation of the anaerobic digester in the present invention. Such a system prevents the buildup of foam inside the digester 30 by spraying liquid preferably continuously onto the upper surface of the mixed liquor in the digester. Such spray preferably covers the majority or substantially all of the liquid surface. The impact of the sprayed liquid on the surface of the liquid level serves to collapse the foam and inhibit foam buildup. Preferably, the liquid sprayed would be mixed liquor from the digester 30. As shown in FIG. 1, at least one spray head 31 is used, and preferably many such spray heads. This defoaming spray system can be supplemented if necessary with conventional chemical defoamer injection, activated through an appropriate foam sensor, and/ or with conventional mechanical methods for foam destruction.

The foregoing detailed description refers to the preferred embodiments of the present invention. However, the apparatus according to the invention is operable when generally comprising a digester; any suitable mixing device capable of inducing a circulation and contributing to an improved mass transfer rate, including but not limited to the examples discussed above; and any suitable shearing device capable of fracturing the solids and introducing them into the digester, including but not limited to the examples discussed above.

Figure 6:
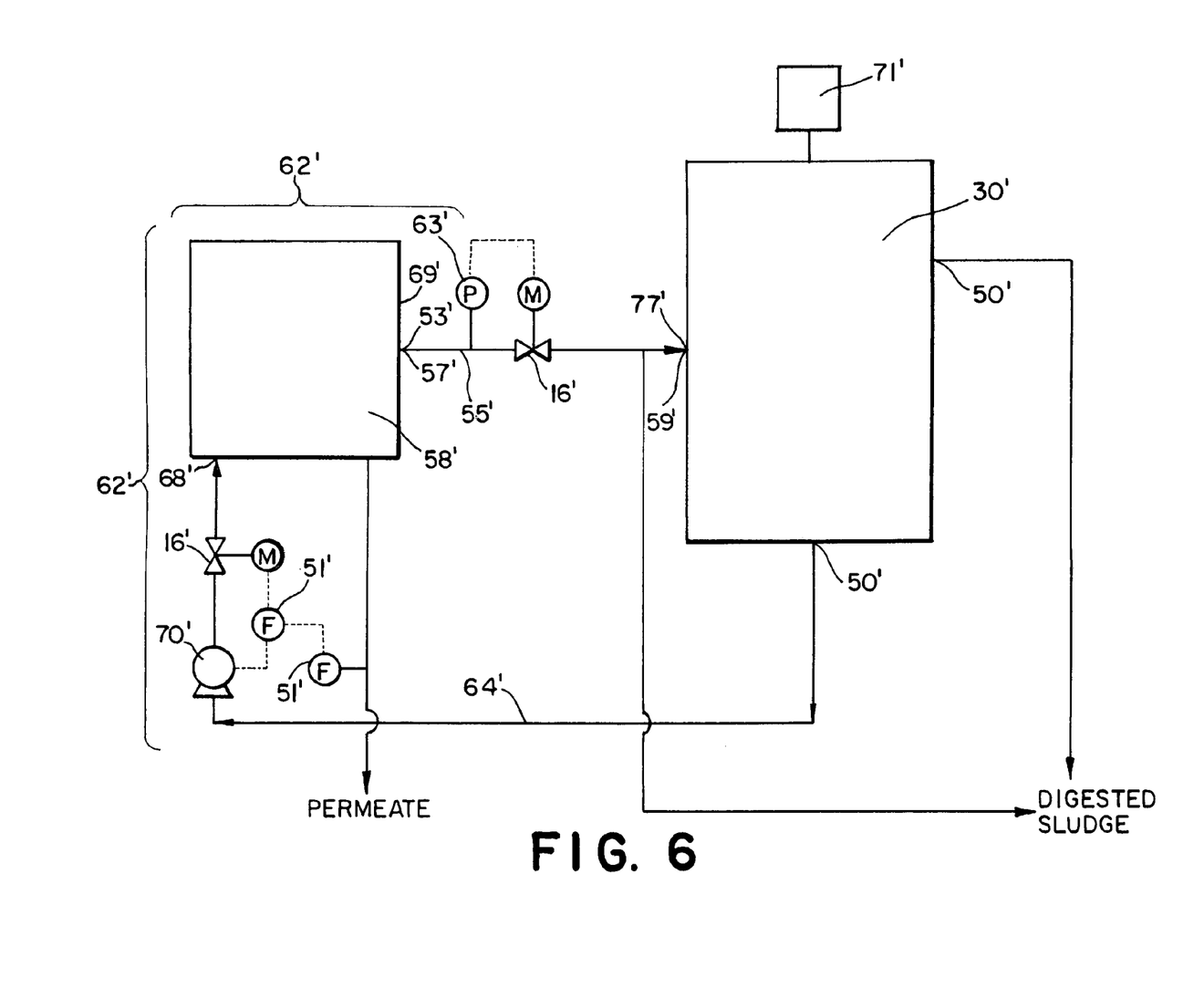
FIG. 6 is a schematic representation of an alternative anaerobic digestion apparatus and a concentrator.

The area delineated by the dashed rectangle in FIG. 5 may be replaced by the apparatus shown FIG. 6. FIG. 6 is directed to an alternative embodiment of the invention comprising a digester, preferably an anaerobic and shear enhanced digester, coupled with a concentrator. The apparatus has improved efficiency due to concurrent operation of the digester and a concentrator. The apparatus includes a digester 30' preferably including a shear source 71', such as a shearing nozzle, a Venturi nozzle, an impeller, or some other device capable of imparting shear to the mixed liquor within the digester, and a concentrator 62' in fluid communication with a mixed liquor inlet 77' of the digester and at least one mixed liquor outlet 50' of the digester 30'. The digester 30' may be the digester 30 above or any digester preferably with a source for imparting shear to the mixed liquor in the digester. If used, the shear source 71' may be either within or outside of the digester 30' or in fluid communication with the digester 30' so long as it is configured to impart shear to the mixed liquor within the digester. The concentrator 62' may be any concentrator that reduces the amount of water in the waste stream, including any of the concentrators 62 described above with respect to FIG. 5. The concentrator 62' and the digester 30' can be configured as described above with respect to FIG. 5 to effect concurrent concentration and digestion of the mixed liquor. The apparatus may further comprise any of the devices and adopt any configuration described above and will optimize the efficiency, particularly of the anaerobic digestion apparatus. Similar to the concentrator 62 described above, the concentrator 62' may comprise a pump 70' and a separator 58' having an outlet 53' which is in fluid communication with an inlet 77' of the digester and an inlet 68' in communication with a mixed liquor outlet 50' of the digester. The concentrator may also include a conduit 55' with a first end 57' connected to the outlet 53' of the separator 58', and a second end 59' connected to the inlet 77' of the digester 30'. This conduit preferably conveys the concentrate from a concentrate side 69' of the separator 58' back to the digester 30'.

A waste stream may be digested in various embodiments of an anaerobic digestion apparatus, as described herein, by feeding the waste stream into the digester, preferably taking into consideration the parameters discussed above. The biodegradable material in the waste stream may be reacted with anaerobic bacteria to produce a mixed liquor and a biogas. This reaction may be further optimized by any of the methods described above, if desired, including controlling temperature and pH, concentrating the mixed liquor, minimizing the entrainment of gas bubbles, etc. The mixed liquor may be introduced to the digester and any shearing device or method may be used, preferably in communication with an inlet of the digester, and the mixed liquor within the digester may be mixed by any mixing device or method, including those described herein.

The invention will now be described in more detail with respect to the following specific, non-limiting examples.

EXAMPLE I

The data in Table 1 illustrate the improved mass transfer rates of the digester apparatus of the present invention. The pilot apparatus for this study was generally the embodiment of the digester apparatus as depicted in FIG. 1 of the attached drawings, hereinafter referred to as a shear-enhanced anaerobic digester (SEAD digester). The apparatus included one two-phase nozzle, a draft tube, and a gas impingement plate, but not the concentrator. The data additionally indicate the impact of typical polymers on the anaerobic digestion process. The data is taken from a pilot study at a POTW wherein the feed to the SEAD digester was a mixture of primary and secondary sludge that had been thickened using a conventional belt thickener with the addition of polymers. For this study the digester was operated in a once-through mode without a concentrator. During the study the POTW elected to change the type of polymer being used as indicated in the table. At the point indicated in Table 1, the feed to the digester apparatus was changed to a point upstream of the polymer addition and the polymer was purged from the system until it was polymer free.

TABLE 1

| | Date | | | |
| --- | --- | --- | --- | --- |
| Parameter | Month 3 Chem. A | Month 4 Chem. B | Month 5 Purging | Month 6 Purged |
| Feed Conc. (% TS) | 5.1 | 4.1 | 2.3 | 2.2 |
| HRT (days) | 18.1 | 36.4 | 11.4 | 9.5 |
| SRT (days) | 18.1 | 36.4 | 11.4 | 9.5 |
| Bio-activity (kg/kg/d) | 1.3 | 0.7 | 1.3 | 2.0 |
| Rx VFA (meq/L) | 5.0 | 6.9 | 2.3 | 0.6 |

The above data are monthly average operating data. Chemical A is a cationic water soluble polymer in emulsion. Chemical B is a solution mannich polymer. The feed concentration is expressed in percent total solids (% TS), i.e. lbs. of solids per 100 lbs. of liquid sludge. The HRT is hydraulic retention time in days, which in a once-through system equals the solids retention time (SRT). The bioactivity is a measure of the volatile solids conversion capacity of the anaerobic biomass and is expressed as kilograms of volatile solids digested per kilogram of digesting bacteria (volatile solids) per day.

Rx VFA is the concentration of volatile fatty acids in the digester expressed in milliequivalents per liter (meq/L). Rx VFA is a measure of the process stability in the digester. Rx VFA readings of less than 1.0 indicate that the digesting environment is very stable and could likely perform at even higher mass transfer rates.

The first column indicates the data for the last month wherein Polymer A was added. The SRT is roughly equivalent to that of an aggressively designed conventional digester. The VFA indicates less than optimal stability. The second column indicates the data for the subsequent month of operation when the POTW switched to a more economical polymer. Performance of the SEAD digester deteriorated as indicated by the much longer SRT as well as the elevated VFA indicating that Polymer B was significantly more inhibitory than Polymer A.

At this point in the study, the location of the feed was moved to allow the SEAD digester to receive the same sludge mix before thickening and polymer addition. The next column indicates the data for the month during which the SEAD digester was gradually purged of the polymer. The SEAD digester performance increased significantly achieving an SRT below the conventional 20-40 days and with a more stable VFA. The final month of the study reflects the performance of the SEAD digester on the same sludge after the polymer was completely purged from the SEAD system. An SRT of less than 10 days was achieved with a very stable VFA indication. The study was ended before the most optimal SRT achievable for this application was determined, but the very low VFA indicates that further reductions in SRT would likely have been possible.

The effectiveness of the shear enhanced anaerobic digester apparatus according to the invention is illustrated by this data. The improved mass transfer rates allow for sludge digestion to be performed at an SRT that is 50% of the lower design guideline recommended for conventional systems. The study also identifies that the benefits of the SEAD apparatus are best obtained if the feed stock does not contain commonly used polymers in the thickening process.

The data in Table 2 are taken from a pilot study on an industrial waste activated sludge wherein the sludge had been thickened using a conventional thickener with the addition of a cationic polyacrylamide in a water-in-oil emulsion as a polymer. The pilot apparatus for this study was essentially the embodiment depicted in FIG. 1.

TABLE 2

| Parameter | Industrial | High Rate | Egg Shaped |
|---|---|---|---|
| Feed Conc. (% TS) | 4.1 | 4.6 | 5.0 |
| HRT (days) | 12.2 | 26 | 20 |
| SRT (days) | 12.2 | 26 | 20 |
| Bio-activity (kg/kg/d) | 1.2 | 0.6 | 0.8 |
| Rx VFA (meq/L) | 4.5 | 3.7 | N/A. |

Data for Conventional Digesters designated as "High Rate" in Table 2 was taken from WEF (1992): "Manual of Practice No. 8: Design of Municipal Wastewater Treatment Plants Volume II: Chapters 13-20", pp. 1261-1263. ISBN 0-943244-85-4. Data for "Egg-Shaped" Digesters in Table 2 was taken from Brinkman, Doug and Voss, Denton (1999): "Egg Shaped Digesters, are they all they're cracked up to be?" Water Environment & Technology, November Issue, pp. 28-33. Each of these sources of data is hereby incorporated by reference. The SRT of 12.2 days for the SEAD indicates a significant improvement over the design basis SRT for conventional digesters. The elevated VFA indicates that the stability of the system was not optimal. Although no study of the effect of the polymer was undertaken here, without wishing to be bound by any theory applicants herein attribute the elevated VFA at least in part to the inhibitory impact of the polymer on the digestion efficiency The data in Table 3 are taken from a pilot study on a mixture of primary and secondary sludge taken from a POTW system at a point before thickening and polymer addition. The pilot apparatus for this study was essentially as depicted in FIG. 5, with the exception that only one two-phase nozzle and one draft tube were used, hereinafter designated as a membrane coupled shear enhanced digestion apparatus (MCSEAD digester).

TABLE 3

| Parameter | SEAD Only | Transition MCSEAD | Extrapolated MCSEAD |
|---|---|---|---|
| Feed Conc. (% TS) | 0.5 | 0.5 | 0.5 |
| HRT (days) | 11 | 5 | 1 |
| SRT (days) | 11 | 11 | 11 |
| Bio-activity (kg/kg/d) | 1.4 | 2.0 | 1.4 |
| Rx VFA (meq/L) | 0.6 | 2.0 | <1.0 |

The first column indicates the performance obtained on the unthickened feed without the concentrator in operation. The SRT again indicates that the improved mass transfer rates of the SEAD apparatus according to the invention are beneficial to the digestion process. The low VFA indicates that further reductions in SRT might be possible. The concentrator was then activated and the same sludge feed was concurrently concentrated and digested. Concentration was achieved with a membrane separation system without the addition of polymers as indicated in the preferred embodiment. The second column indicates the performance with the concentrator operating during a transition period as the mixed liquor TSS is increasing. As the quantity of digesting bacteria accumulated in the digester, increased demand on the existing bacteria is indicated by the increase in Bioactivity and slightly elevated VFA. When the concentration transition is complete, equilibrium will be restored and the extrapolated results are indicated in column three. Data for the equilibrium condition were not obtained due to mechanical limitations at the pilot scale. The membrane separator performed effectively as evidenced by the reduction of HRT at a constant feed concentration and SRT.

Sludge digester systems are typically once through systems designed based on SRT and HRT. The solids concentration of raw sludge is typically about 1% TS. In order to keep digester volume reasonable, sludge is often thickened to about 5% TS before digestion. Table 2 shows that the embodiment of the digester of the apparatus of the present invention including a shearing device and a mixing device can achieve the same process performance with prethickened sludge as a conventional high rate or egg-shaped digester, but at a considerably reduced SRT and HRT.

Further, Table 1 shows that thickening polymers can be moderately to severely inhibitory to the anaerobic bacteria in the applicants' digester having a shearing device and a mixing device, and that elimination of such polymers improves process stability and bacterial activity. Mere removal of the polymer is not a practical way in which to improve such process stability and bacterial activity because it would require treatment of dilute sludge in such a digester apparatus, which even at reduced SRT and HRT would require a large digester volume. Further, prethickening raw sludge from 1% TS to 5% TS with a membrane separator upstream of the digester is difficult, as discussed above, because the presence of hydrophilic compounds in sludge can prevent efficient performance of the upstream membrane. Accordingly, applicants' embodiment further including concurrent digestion and concentration of the mixed liquor permits control of SRT independently of HRT, making it possible to digest dilute sludge without use of inhibitory polymers and using a digester volume similar to or less than the digester volumes associated with the prethickened sludge as used in Table 2. Table 3 illustrates that for a given digester volume, applicants digester embodiment using the addition of a membrane concentrator according to the invention permits maintaining an SRT of 11 days while increasing the digester throughput by a factor of 11, as shown by the decrease in HRT from 11 days to 1 day.

It will be appreciated by those skilled in the art that changes could be made to the embodiments described above without departing from the broad inventive concept thereof. It is understood, therefore, that this invention in not limited to the particular embodiments disclosed, but is intended to cover modifications within the spirit and scope of the present invention defined by the appended claims.

We claim:

1. A method for digesting a waste stream in an anaerobic solids digestion apparatus comprising:
    (a) feeding a waste stream comprising anaerobically biodegradable solids to a digester;
    (b) digesting the anaerobically biodegradable solids in the waste stream with anaerobic bacteria in the digester to reduce the biodegradable solids by an amount, thereby producing a mixed liquor and a biogas, wherein the biogas is a product of anaerobic digestion;
    (c) introducing at least a portion of the mixed liquor to the digester through a shearing device that comprises a nozzle having a nozzle gas inlet; and
    (d) mixing the mixed liquor with the remaining anaerobically biodegradable solids in the digester,
    wherein the method further comprises removing a portion of the biogas from the digester and introducing the portion of the biogas into the nozzle gas inlet, and the biodegradable solids are sheared to achieve a sludge retention time (SRT) of less than 20 days.

2. The method according to claim 1, wherein the mixed liquor flows through the nozzle in a generally annular space defined by an exterior surface of a gas flow tube positioned within the nozzle and an interior surface of the nozzle.

3. The method according to claim 1, further comprising introducing the portion of the biogas and mixed liquor from the nozzle into a draft tube within the digester and mixing the portion of the biogas and mixed liquor, thereby inducing internal circulation within the digester as the biogas and mixed liquor flow downwardly through the draft tube.

4. The method according to claim 1, further comprising concentrating the liquor.

5. The method according to claim 4, wherein the steps of digesting the anaerobically biodegradable solids and concentrating the mixed liquor occur concurrently.

6. The method according to claim 1, wherein the method minimizes the need for use of a polymer that inhibits biological activity in a waste stream.

7. The method according to claim 1, further comprising maintaining a mixed liquor pH of about 6 to about 8.

8. The method according to claim 1, further comprising maintaining a mixed liquor temperature of about 80° F. (25° C.) to about 105° F. (40° C.).

9. The method according to claim 1, further comprising maintaining a mixed liquor temperature of about 125° F. (50° C.) to about 145° F. (60° C.).

10. The method according to claim 1, further comprising minimizing the entrainment of gas bubbles in the recirculation system.

11. The method according to claim 1, further comprising venting biogas from the gas collection area of the digester.

12. The method according to claim 1, further comprising minimizing foam in the digester.

13. The method according to claim 1, further comprising removing scum from the digester.

14. A method for improving the efficiency of an anaerobic solids digestion apparatus comprising:
    (a) feeding a waste stream comprising anaerobically biodegradable solids to a digester;
    (b) digesting the anaerobically biodegradable solids in the waste stream with anaerobic bacteria in the digester to reduce the biodegradable solids by an amount, thereby producing a mixed liquor and a biogas, wherein the biogas is a product of anaerobic digestion;
    (c) imparting a shearing force to the mixed liquor in the digester using a nozzle having a nozzle gas inlet; and
    (d) concentrating the mixed liquor, wherein the steps of digesting the anaerobically biodegradable solids and concentrating the mixed liquor occur concurrently, and the method further comprises removing a portion of the biogas from the digester and introducing the portion of the biogas into the nozzle gas inlet, and wherein the nozzle shears the biodegradable solids to achieve a sludge retention time (SRT) of less than 20 days.

15. A method for improving the efficiency of an anaerobic solids digestion apparatus comprising:
    (a) feeding a waste stream comprising anaerobically biodegradable solids to a digester;
    (b) digesting the anaerobically biodegradable solids in the waste stream with anaerobic bacteria in the digester to reduce the biodegradable solids by an amount, thereby producing a mixed liquor and a biogas, wherein the biogas is a product of anaerobic digestion;
    (c) imparting a shearing force to the mixed liquor in the digester using a shearing device that comprises a nozzle having a nozzle gas inlet; and
    (d) mixing the mixed liquor within the digester, wherein the nozzle shears the biodegradable solids to achieve a sludge retention time (SRT) of less than 20 days.

16. The method according to claim 15, wherein the mixed liquor flows through the nozzle in a generally annular space defined by an exterior surface of a gas flow tube positioned within the nozzle and an interior surface of the nozzle.

17. The method according to claim 16, further comprising introducing the portion of the biogas and mixed liquor from the nozzle into a draft tube within the digester and mixing the portion of the biogas and mixed liquor, thereby inducing internal circulation within the digester as the biogas and mixed liquor flow downwardly through the draft tube.

18. The method according to claim 15, further comprising concentrating the liquor.

19. The method according to claim 18, wherein the steps of digesting the anaerobically biodegradable solids and concentrating the mixed liquor occur concurrently.

20. The method according to claim 15, wherein the method minimizes the need for use of a polymer that inhibits biological activity in a waste stream.

21. The method according to claim 15, further comprising maintaining a mixed liquor pH of about 6 to about 8.

22. The method according to claim 15, further comprising maintaining a mixed liquor temperature of about 80° F. (25° C.) to about 105° F. (40° C.).

23. The method according to claim 15, further comprising maintaining a mixed liquor temperature of about 125° F. (50° C.) to about 145° F. (60° C.).

24. The method according to claim 15, further comprising minimizing the entrainment of gas bubbles in the recirculation system.

25. The method according to claim 15, further comprising venting biogas from the gas collection area of the digester.

26. The method according to claim 15, further comprising minimizing foam in the digester.

27. The method according to claim 15, further comprising removing scum from the digester.

* * * * *